United States Patent [19]
Pfau

[11] Patent Number: 5,800,164
[45] Date of Patent: Sep. 1, 1998

[54] SYSTEM TO SELECT THE FORM AND COLOR STRUCTURE OF TEETH

[76] Inventor: Gerhard Pfau, Nieratzer Weg 35, D-88239 Wangen, Germany

[21] Appl. No.: 668,441

[22] Filed: Jun. 21, 1996

[30] Foreign Application Priority Data

Mar. 21, 1996 [DE] Germany .................. 196 11 122.6

[51] Int. Cl.$^6$ ............................ A61C 19/10; A61C 13/08
[52] U.S. Cl. ........................................ 433/26; 433/203.1
[58] Field of Search ........................... 433/26, 203.1, 433/215, 218, 229

[56] References Cited

U.S. PATENT DOCUMENTS

| | | | |
|---|---|---|---|
| 1,338,068 | 4/1920 | Bush | 433/26 |
| 5,308,243 | 5/1994 | Emmons | 433/203.1 |
| 5,482,459 | 1/1996 | Yarovesky et al. | 433/26 |
| 5,624,262 | 4/1997 | Yarovesky et al. | 433/203.1 |

*Primary Examiner*—Nicholas D. Lucchesi
*Attorney, Agent, or Firm*—Dority & Manning

[57] ABSTRACT

The present invention deals with a system for the selection of form and color structure of teeth, in particular for application in the preparation and production of ceramic or plastic-composition faced tooth replacements. The system consists of several assortments comprising models and image representations as well as layering diagrams of different tooth forms and tooth color structures. A comparison of form and color between the patient's teeth and the models is then made, whereby the suitable assortment(s) are selected and can be reproduced true to nature in the dental laboratory, using the appertaining layering diagrams. The system according to the invention consists of several components which can be assembled to form a basic assortment.

8 Claims, 4 Drawing Sheets

SYSTEM TO SELECT THE FORM AND COLOR STRUCTURE OF TEETH

BACKGROUND OF THE INVENTION

The invention relates to a system to select the form and color structure of teeth, in particular for application in the preparation and production of tooth replacements.

The method used until now to determine the color structure is based on color scales with e.g. 20 color samples containing the most common natural tooth colors. The dentist or dental technician determines the tooth color suitable for the patient by comparing the color scales with the patient's tooth color, so that the reproduction of the tooth with ceramic compositions or synthetic facing compositions can be produced by the manufacturer from a basic assortment. The incorporation of the color impression into the tooth replacement to be produced is effected by means of a simple layer technique when applying the facing compositions, whereby as a rule five compositions of the basic assortment are used, being applied generally in the following sequence on the basic body of the tooth replacement:

Opaquer, opaque dentine, dentine, cutting composition and transparent composition.

Only the basic color of the tooth can be reproduced with these compositions of course, with naturally occurring color characteristics such as light/dark inclusions, e.g. secondary dentine, calcium spots, mamelons or an incisal seam of another color can only be achieved by applying so-called effect compositions. In order to reproduce the natural tooth image, the dental technician must prepare individual sketches in which he notes the appropriate color characteristics of the patient's tooth, the effect compositions and layer techniques that must be used in his own experience.

The problem here is the precise color notation from the Patient and the application of the effect compositions, where only long experience and much testing makes it possible to evaluate the color effect obtained in the finished tooth replacement.

In order to learn color determination and special effect composition and layering techniques, a great outlay of money and time is necessary.

The reproduction of the natural tooth form is also fraught with problems, especially when the patient already wears tooth replacement, i.e. when the original natural tooth form is not known. The dental technician then has practically no basis for shaping the form of the tooth replacement.

OBJECTS AND SUMMARY OF THE INVENTION

It is a principal object of the present invention to make possible simple and safe determination of the tooth form and of the color structure and to render the found form and color characteristic reproducible in as close-to-nature a manner as possible. Additional objects and advantages of the invention will be set forth in part in the following description, or may be obvious from the description, or may be learned through practice of the invention.

Different assortments are provided, containing models and pictures as well as layering diagrams for different tooth forms and tooth color structures. The form and the color structure of the patient's teeth is compared with the models, whereby the suitable assortment(s) are selected in the simplest manner possible and can be reproduced faithfully and true-to-nature in a dental laboratory.

The system according to the invention consists of different component which can be brought together to form a basic assortment. The most important components are:

Situation model(s) of the upper and/or lower jaw of a subject.

Color image representation of the buccal situation of a subject

Layering diagrams associated with the color images for step-by-step representation of the necessary layer sequence for the reproduction of the tooth replacement.

The following basic assortments are set up:

1. Basic assortment, front teeth (for laboratory)
2. Master assortment(s), front teeth (for laboratory)
3. Lateral tooth assortment(s) (for laboratory)
4. Imaged representation of the layering procedure and layering technology (for the laboratory)
5. Dentist's assortment
6. Computer program (optional)

1. Basic Assortment:

The basic assortment consists of several sets and a collection of images (photographs, slides) associated with same. The different sets always contain situation models of the natural teeth of a subject, in particular front teeth (upper jaw, lower jaw), photographs (slides) and a layering diagram of the applicable patient example. Instead of the situation models, it is also possible to use tooth models made of layered ceramic or plastic facing material. The models may be provided with metallic surfaces if so desired.

One or several sets of the basic assortment can also contain situation models showing past restoration of individual teeth instead of the situation model of the natural teeth of a subject, whereby the restoration was carried out in accordance with the process of the invention. In this case the sets also contain the images and layering diagrams fitting the restored teeth of the situation models.

The situation models represent the exact tooth situation in the subject's mouth. The imaged representations show the mouth situation in close-up and are taken by direct color photography and mirror photographs, and are a faithful rendition of the dental situation of the subject in question, reflecting the individual character of the teeth. In order to make possible a reproduction by means of a ceramic system or plastic facing system, the applicable layering diagram for the subject is provided on transparencies which can be superimposed on each other or through detailed description in book or notebook form with text and color photographic material showing the applicable layering diagram for the subject from which the methodical manner of proceeding can be recognized concerning the selection of facing and effect compositions, and to what depth and in what areas they are to be used in order to reproduce the natural color effect. The result of a reproduction produced according to the present process can be documented photographically and can be included.

For this, blank layering diagrams are also supplied, to make it possible to note color differences in patient cases with identical diagrams. The basic assortment consists of subject examples covering the most frequently found characteristics of tooth forms and tooth colors. The assortment is conceived for work in the laboratory and is an always available model for the dental technician in dealing with color and form determination for teeth and their true-to-nature reproduction by means of the applicable ceramic or plastic facing system.

2. Master Assortment(s)

The master assortment is structured as the basic assortment and has the same application. The difference from the basic assortment lies in the selection of the subject examples. The master assortment contains extraordinary form color and positioning examples such as:

Strong secondary dentine formation, possible discoloration due to drugs or other extraordinary, naturally occurring color structures.

3. Lateral Teeth Assortment(s)

The make-up of the lateral teeth assortment is the same as for the master or basic assortment, with the difference that all the parameters taken into account in the assortments mentioned above relate to application to lateral teeth.

A collection of plaster or plastic duplicates obtained from natural individual teeth is included with the assortment for the study and comparison of natural chewing surfaces and crown reliefs. In order to obtain chewing surfaces, silicon forms of same are available.

4. Image Representation (photographs, slides) of the Ceramic Layering Method.

With reference to the basic, master and lateral tooth assortment, the build-up of the ceramic compositions is documented for each set step by step on image supports. The ceramic compositions or plastic facing compositions are colored differently, and together with the layering diagram, the dental technician can reproduce step by step the procedure for the reproduction of the color situation for the applicable subject.

5. Dentist's Assortment(s)

The dentist's assortment has the same composition and contents as the basic, master and lateral tooth assortment. It enables the dentist to determine directly with the patient his tooth form, tooth color and position. Using the enclosed color photographs and/or slides it is possible to determine the characteristics of a patient's teeth and, if necessary, to note the ceramic compositions or plastic facing compositions or effect compositions to be used in reproduction on the blank diagram.

6. Computer Program (optional):

The task of a supported computer program may be:

the representation of the situation models of the assortments on the screen or corresponding display devices Image representation of the assortments Representation of the layering diagrams of the assortments Representation of blank diagrams Representation of the layering method.

The possible functions of a computer program may be:

Representation of the above-mentioned parameters and their links, so that each layering diagram is combined with every form of the situation models.

Changes in the color structure of each layering diagram, i.e. the color selection according to the blank layering diagram is entered in the stored layering diagram. The result of the color changes is processed by the program and the corresponding image is transmitted and the effect on the color overall impression appears on the screen. The possibility exist of expressing the image representation in color.

Change of form and position of the teeth

Scanning of treatment cases of photographs or videos and representation of the layering diagram to be used by the dental technician and the facing compositions or effect compositions required for this.

The system according to the invention, thanks to a great number of examples of tooth forms and color structures explaining the process through layering diagrams and image representation which explain the process, and thanks to images of the results of this layering method, provides optimal communication between dentist and dental laboratory with good reproducibility of the tooth replacement to be supplied. By combining the tooth forms and layering diagrams of different sets, the dentist and the dental technician obtain a plurality of application possibilities in order to provide an individual tooth replacement suited to the patient.

The invention is explained through drawings below, which merely show an embodiment. Additional characteristics and advantages of the invention appear from the drawings and their description.

DETAILED DESCRIPTION OF THE PREFERRED EMBODIMENTS

Figure 1:
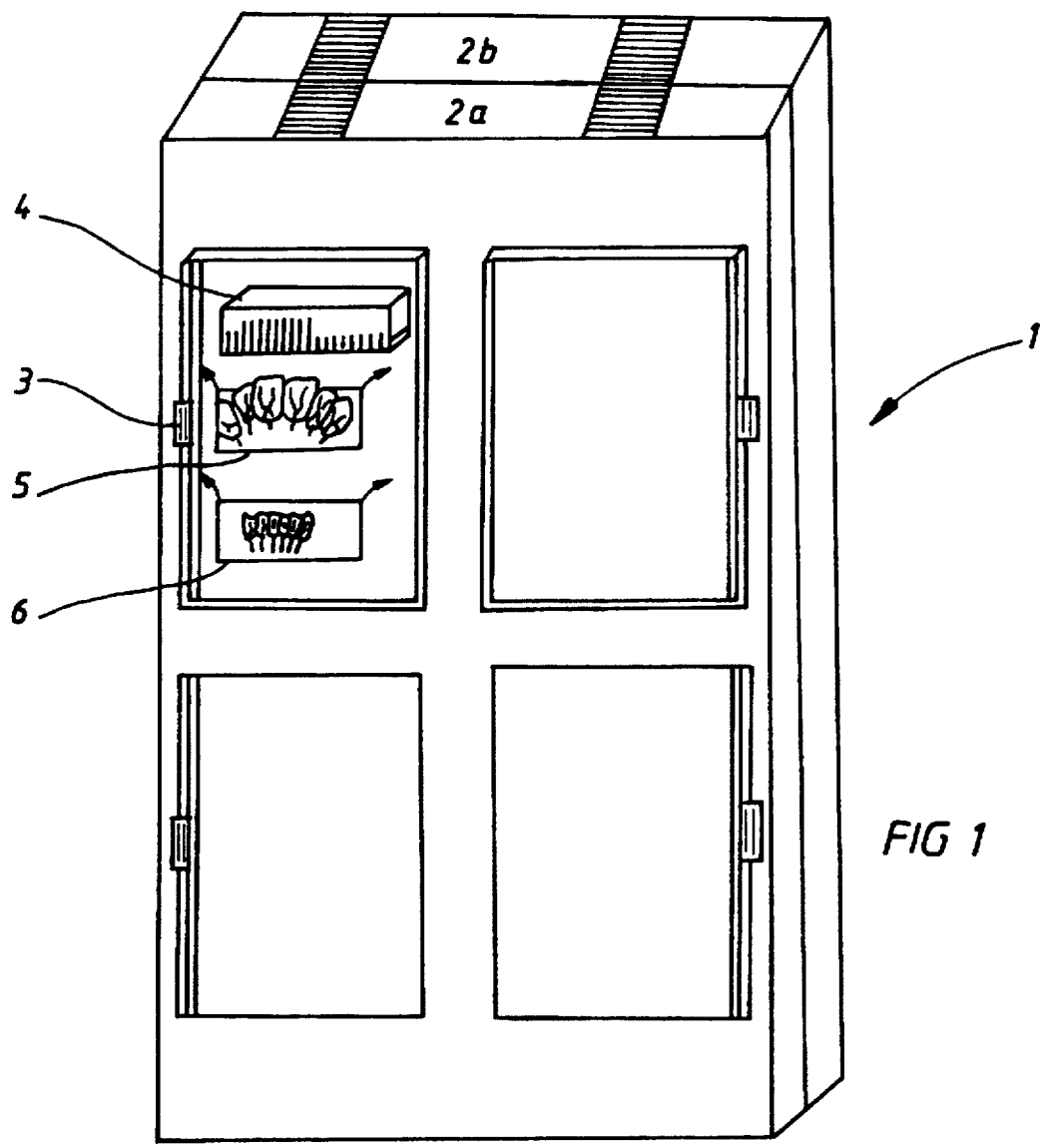
FIG. 1 shows an example of an embodiment for the build-up of the system according to the invention.

Reference will now be made in detail to the presently preferred embodiments of the invention, one or more examples of which are shown in the drawings. Each example is provided by way of explanation of the invention, and not as a limitation of the invention. For example, features illustrated or described as part of one embodiment can be used on another embodiment to yield a still further embodiment.

Figure 2:
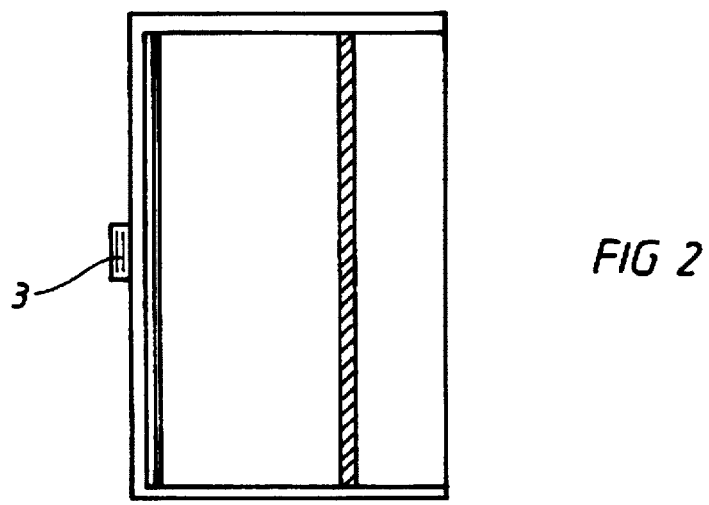
FIG. 2 shows the drawer schematically, in an enlarged view.

FIGS. 1 and 2 show an example of how the system can be structured for form and color determination of teeth in practical application. The assortments are provided in a detachable, stackable container 1 which in the example consists of two elements 2a, 2b, but may also comprise more elements. Each element 2 comprises e.g. four sets with one subject example for each and with drawers 3. Four images (slides) are contained in a removable box in the sets, the upper and lower jaw situation 5, 6 on a removable pedestal platform and a drawer 3 containing the pertinent documentation and the appertaining layering diagrams.

The assortment 1 may consist of two or more elements 2, so that in the example a total of eight form and color situations are present which can be combined with each other, and through combination of the models and layering diagrams with images of different sets, a total of 36 different upper-jaw situations and 36 different lower-jaw situations are possible.

Container 1 shows the basic assortment for example, which may be completed by additional elements 2 containing one or more master assortments. The basic tooth color selection is made in the conventional manner, e.g. using the color code of the Ducera company.

The tooth form and color structure selection, i.e. individual, color and form characterization of the teeth, is made through the models and the image material of the different sets. Here the following basic characteristics can be differentiated, for example: Tooth form, tooth color, basic tooth body, tooth collar, possible mamelons, possible incisal seam (seam at the cutting edge), cutting range.

In addition to the ceramic compositions used in general: Opaquer, opaque dentine, dentine, cutting composition, a plurality of effect compositions are used which are obtainable in all the naturally occurring color gradations. These are usually designated according to their color effect, e.g. opal, flamingo, blue, amber (e.g. from modifier and opal composition assortments of the Ducera Dental Company, Rosbach).

The color selection is made as a rule by the dentist, using the conventional color scales. Using the situation models contained in sets No. 1 to No. 8, a tooth form coming closest to the patient's original tooth form can be found, e.g. the tooth form from set No. 7.

The selection of the individual characteristic (e.g. mamelons, secondary dentine) is made using the image material of the dentist's assortment. The selection of the color effect of the individual characteristics is made by using single-composition color scales (e.g. of the modifier compositions) and are noted according to FIG. 3 on the blank diagrams. The shown incisor of the patient has e.g. a color structure according to set No. 3, i.e. a tooth color 8 which deviates from the color of the basic body 7, an incisal seam 10, three mamelons 9 and one color-altered cutting edge 11. In addition to these individual characteristics, the appropriate color scheme must now be selected by using the color diagrams shown in photographs or slides. For example, the color of the basic body: A3, tooth collar colar: Amber, color of the incisal seam: blue opal, color of the mamelons: flamingo, color of the cutting edge: S59.

Figure 3:
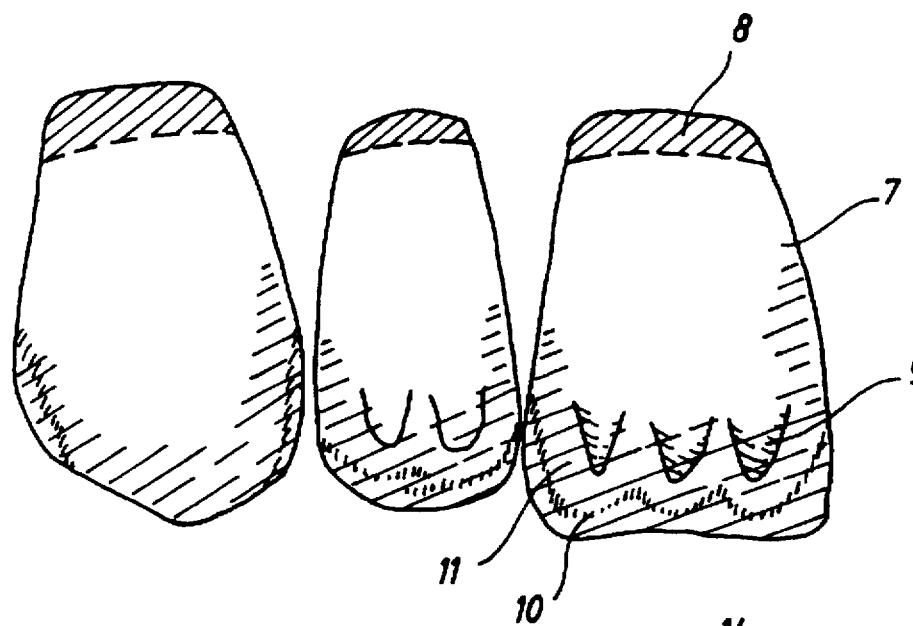
FIG. 3 shows an example for the color characteristics of natural teeth.

This color scheme is already contained in an example of the assortment (e.g. set No. 3), and a deviation of the color effect must be noted by the dentist himself on a blank layering diagram (FIG. 3).

The dental laboratory which is given the order, receives the data collected by the dentist in appropriate form: E.g.: patient 12345: tooth color A3, tooth form: Set No. 7, tooth color structure Set No. 3, color value: set No. 5 (or, in case no suitable color scheme has been found: color of the basic body A3, color of tooth collar: amber, incisal seam: blue opal, mamelons: flamingo, cutting edge: S 59 according to blank layering diagram).

The dental technician gathers the corresponding situation models, color diagrams, layering diagrams and images from the basic or master set and thus obtains a precise model for the production of the tooth replacement, with step-by-step instructions.

Figure 4A:
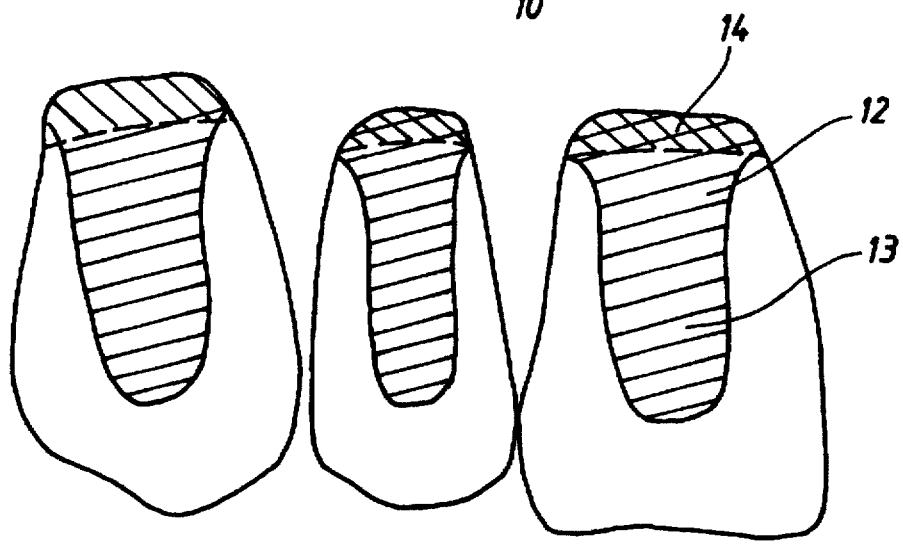
FIGS. 4a to 4d show examples for the layering method step by step, in order to obtain the desired color effect (layering diagram) relating to FIG. 3.

According to FIGS. 4a to 4d, according to the layering diagram in a first step, a metal cap 12 which forms the base for the tooth replacement is surrounded by opaquer composition 13: color A3. The collar of the tooth 8 is graduated in color by intensive opaquer 14: color red-brown (FIG. 4a).

Figure 4B:
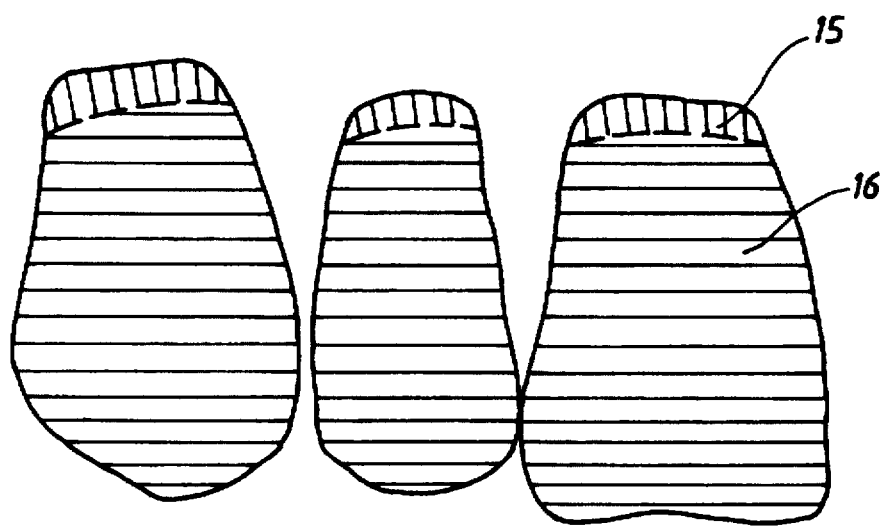

The second step consists in providing the tooth with a layer of dentine 16 and to bring it into its required form. Here the tooth collar 8 must again be graduated in color with a special effect composition 15 according to the layering diagram. (FIG. 4b).

Figure 4C:
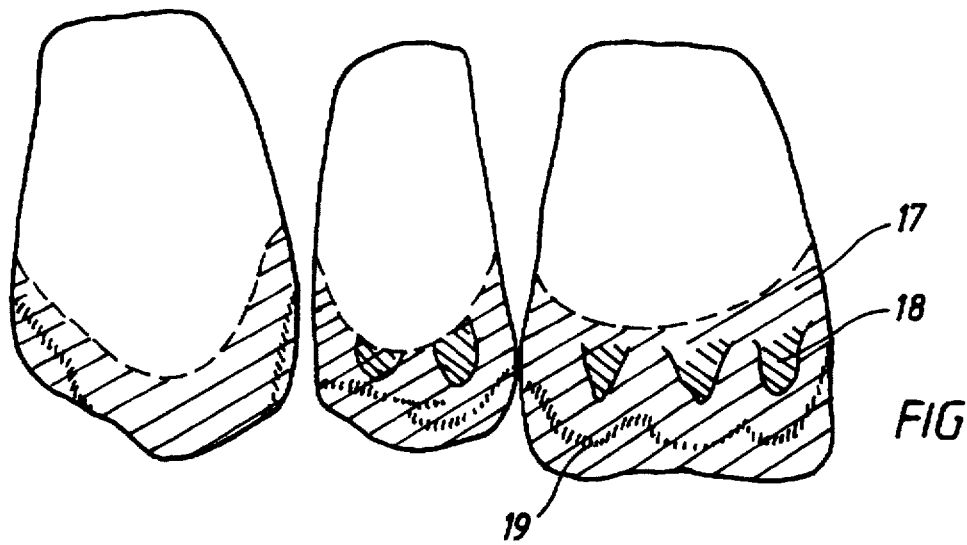

In a third step, the dentine layering 16 is now reduced in the area of the found color inclusions, mamelons 9 and in the area of the incisal seam 10. The mamelons 9 are layered by means of an effect composition layer 18 of the required color. In the same manner, a suitable effect composition layer 19 is applied in the area of the incisal seam 10. The entire tooth replacement is covered in the area of the cutting edge with cutting composition 17 (FIG. 4c).

Figure 4D:
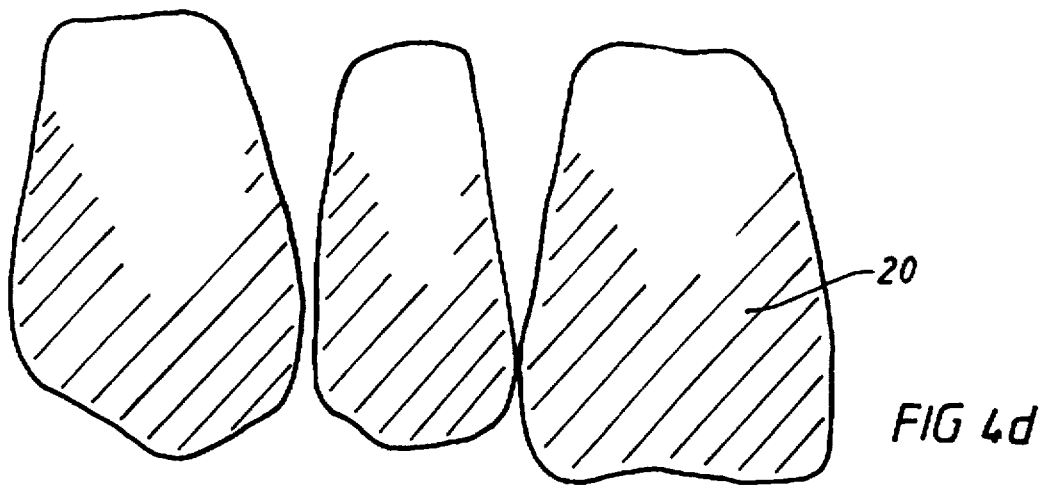

In the fourth step the area of the cutting edge 11 is covered with a covering layer made of a transparent composition 20 (FIG. 4d).

Figure 5:
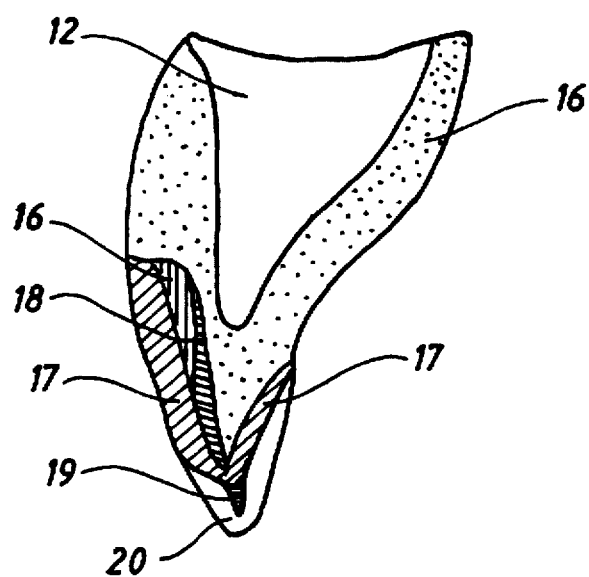
FIG. 5 schematically shows the layering method in a section, as related to FIGS. 3 and 4a to 4d.

FIG. 5 again shows the layering method according to the example, in a section.

Figure 6:
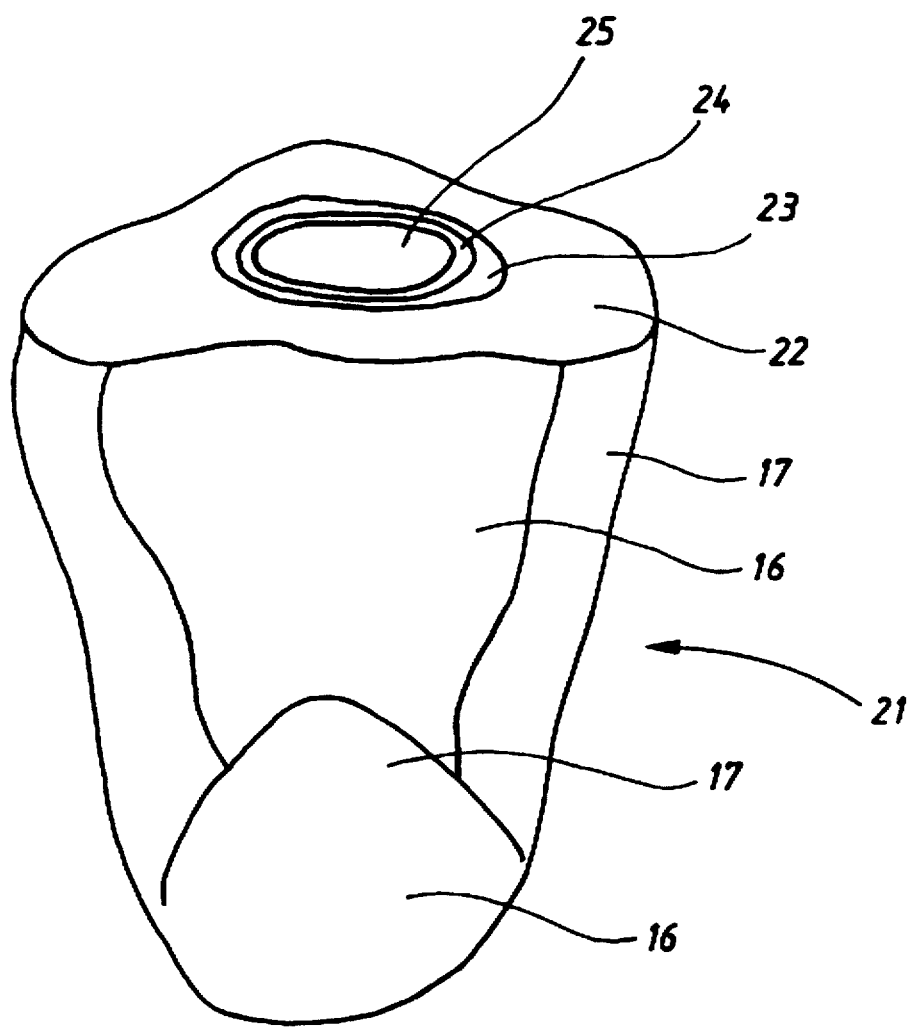
FIG. 6 schematically shows the layer structure of an upper palatinal molar.

FIG. 6 shows an example of layering a palatinal molar. The basic tooth body 21 is formed from a dentine composition 16 and a cutting composition 17 and in the area of the incisal portion, the cutting composition 22 is applied. Approximately in the center of the incisal area, an area is filled with a secondary dentine composition 25 which is of a yellowish-brown coloration. Around the area of the secondary dentine, two layers of effect compositions 23, 24 are shown, e.g. with a slightly whitish component 24 and a bluish component 23.

It will be apparent to those skilled in the art that various modifications and variations can be made in the present invention without departing from the scope and spirit of the invention. It is intended that the present invention cover such modifications and variations as come within the scope of the appended claims and their equivalents.

I claim:

1. A system for the selection of form and color structure of teeth replacements, said system comprising:

at least one situation model of the upper or lower jaw of a subject;

color image representations of a mouth situation of said subject;

layering diagrams associated with said color image representations; and instructions for a step-by-step layering sequence of said layering diagrams for production of a tooth replacement for said subject.

2. The system as in claim 1, further comprising color image representations of said layering sequence according to said layering diagram.

3. The system as in claim 1, further comprising blank diagrams for individual determination of tooth color characteristics.

4. The system as in claim 1, further comprising reproductions of said subject's individual natural teeth providing examples of natural tooth form and chewing surfaces.

5. The system as in claim 4, further comprising silicone forms of said chewing surfaces.

6. The system as in claim 1, wherein said situation models comprise models of existing teeth of said subject.

7. The system as in claim 1, further comprising image representations of teeth reconstructed in accordance with said layering diagrams.

8. The system as in claim 1, further comprising a computer system configured for simulation of said layering sequence of said layering diagrams on said situation model.

* * * * *